United States Patent
Pasqualini et al.

(10) Patent No.: US 6,469,146 B1
(45) Date of Patent: Oct. 22, 2002

(54) RADIOPHARMACEUTICAL PRODUCTS SUITABLE FOR THE SELECTIVE LABELING OF LYMPHOCYTES, AND THEIR PREPARATION

(75) Inventors: Roberto Pasqualini, Clanart (FR); Emmanuel Bellande, Saulx les Chartreux (FR); Franck Mevellec, Rennes (FR); Alain Roucoux, Rennes (FR); Nicolas Noiret, Saint Sulpice la Foret (FR); Henri Patin, Rennes (FR)

(73) Assignee: Cis Bio International, Saclay (FR)

( * ) Notice: Subject to any disclaimer, the term of this patent is extended or adjusted under 35 U.S.C. 154(b) by 0 days.

(21) Appl. No.: 09/584,108

(22) Filed: May 31, 2000

(51) Int. Cl.$^7$ ................................................. C07F 13/00
(52) U.S. Cl. ..................... 534/14; 424/1.65; 424/9.1; 424/1.11; 549/34; 549/89
(58) Field of Search ................... 534/7, 10–16; 424/1.77, 1.65, 1.11, 9.1; 549/1, 29, 30, 34, 59, 62, 66, 88, 89; 206/223, 569, 570

(56) References Cited

FOREIGN PATENT DOCUMENTS

FR     2 698 272     5/1994

OTHER PUBLICATIONS

C. A. McConnachie, et al., Inorg. Chem., vol. 38, No. 5, pp. 964–972, "Ligand and Tetrathiometalate Effects in Induced Internal Electron Transfer Reactions", 1999.

K. Uno, et al., Radiolabeled Blood Elements, pp. 261–265, "111In Labeled Lymphocyte Scintigraphy In Patients With Malignant Lymphoma", 1994.

A. Signore, Radiolabeled Blood Elements, pp. 267–271, "In Vivo Detection of Lymphocytic Infiltration: Present Status and New Prospects", 1994.

F. Demaimay, et al., Nuclear Medicine & Biology, vol. 24, pp. 439–445, "New Bis(Dithiocarboxylato) Nitridotechnetium–99M Radiopharmaceuticals for Leucocyte Labelling: In Vitro and In Vivo Studies", 1997.

F. Demaimay, et al., Nuclear Medicine & Biology, vol. 26, pp. 225–231, "Studies of Technetium–99M Nitridobis-dithiocarboxylate Leucocyte Specific Radiopharmaceutical: [$^{99M}$Tc(DTCX)$_2$], DTCX=CH$_3$(CH$_2$)$_8$CS$_2$. The Cellular and Subcellular Distribution in Human Blood Cells, and Chemical Behaviour. Synthesis of the Analogous Rhenium–188 Radiopharmaceutical", 1999.

C.A. McConnachie, et al., American Chemical society, Inorganic Chemistry, vol. 36, pp. 6144–6145, "A New Sulfur–Rich Rhenium(III) Complex, Re(S$_2$CC$_6$H$_5$)(S$_3$CC$_6$H$_5$)$_2$, and Seven–Coordinate Complexes Formed by Reversible Sulfur Abstraction Reactions, Re(S$_2$CC$_6$H$_5$)$_3$(PPh$_3$) and [RE(S$_2$CC$_6$H$_5$)$_3$(CN)]", 1997.

Franck Mévellec, et al., Inorganic Chemistry Communications 2, pp. 230–233, "Synthesis and Characterization of the Bis (Trithioperoxybenzoate) (Dithiobenzoate) Rhenium (III) Hetero Complex", Jun. 1999.

*Primary Examiner*—Dameron L. Jones
(74) *Attorney, Agent, or Firm*—Oblon, Spivak, McClelland, Maier & Neustadt, P.C.

(57) ABSTRACT

The invention concerns radiopharmaceutical products suitable for the selective labeling of lymphomas containing a metal complex with the formula:

$$[M(R^1CS_2)(R^1CS_3)_2]$$

in which M is chosen from among $^{99m}$Tc, $^{186}$Re and $^{188}$Re, and $R^1$ represents an alkyl, cycloalkyl, aralkyl or aryl group, optionally substituted, obtained by reaction of a pertechnetate or a perrhenate with a reducing agent such as SnCl$_2$ZP$_2$O in the presence of a dithiocarboxylate having the formula: $(R^1CS_2)^-Z_2^+$.

17 Claims, No Drawings

RADIOPHARMACEUTICAL PRODUCTS SUITABLE FOR THE SELECTIVE LABELING OF LYMPHOCYTES, AND THEIR PREPARATION

TECHNICAL FIELD

The subject matter of the present invention is a radiopharmaceutical product using radioactive metal complexes for the selective labeling of lymphocytes.

Such radioactive products are suitable in particular for the diagnosis of inflammatory processes and of malignant lymphomas, and for radiotherapy of malignant lymphomas.

PRIOR ART

Radiolabeled products used for these diagnoses and therapies are described in particular in the work: Radiolabeled Blood Elements, published by J. Martin-Conin, Plenum Press, New-York, 1994, pages 261 to 263 [1] and pages 265 to 271 [2].

In these documents, lymphocytes labeled with $^{111}$In-oxinetropolone, lymphocytes labeled with $^{99m}$Tc-HMPAO, nanocolloids labeled with $^{99m}$Tc-HSA, polyclonal human immunoglobulins or monoclonal antibodies are used.

These techniques do not give satisfactory results since it is necessary firstly to separate the lymphocytes from whole blood in order to label them with appropriate products.

More recently, it has been found that radiopharmaceutical products containing bis(dithiocarboxylato)-nitrurotechnetium-99m could be used to achieve selective labeling of leukocytes, and studies have been made on the influence of the hydrocarbon chain of the ligand on the results obtained, as described in Nuclear Medicine & Biology, 1997, volume 24, pages 439–445 [3] and 1999, volume 26, pages 225–231, [4]. Radiopharmaceutical products of this type are of great interest since when they placed in the presence of blood cells (erythrocytes, leukocytes, platelets) these radioactive complexes show selective affinity for leukocytes. Also, document [4] showed that the complex $[^{99m}TCN(CH_3)(CH_2)_8CS_2)_2]$ also has selectivity for lymphocytes.

Contrary to radiolabeled granulocytes, which are routinely used in clinical practice to detect sites of infection and/or inflammation, radiolabeled lymphocytes have been little used either for diagnostic or for therapeutic purposes.

This is due to the combination of several technical or basic difficulties. Among operative difficulties, the need must be taken into account to make prior separation, before radiolabeling, of the lymphocytes from the other blood cells in whole blood, in particular from the granulocytes.

Despite the difficulties mentioned, radiolabeled lymphocytes could be used in man for improved diagnosis and for improved therapeutic management of diseases characterized by chronic inflammation.

Also, recently published results have shown that malignant lymphomas, in particular non-Hodgkin's lymphoma, could be successfully treated by radioimmunotherapy, a technique which consists of using a monoclonal antibody radiolabeled with β$^-$ ray emitters having a strong affinity for malignant lymphocytes. In this way the lymphocytes are radiated by the β$^-$ ray emission of the radioelement vectored by the antibody which binds itself to the surface of the cells. Radioimmunotherapy of lymphomas, however, encounters various difficulties, including the use of large quantities of non-labeled antibodies to saturate the high number of antigen sites present on the cells. The cost of treatment is therefore greatly increased. In addition, there is a risk that the injection of the first therapeutic dose may cause an immunity reaction which creates human antibodies directed against the antibodies used for treatment (anti-antibodies). If a second therapeutic dose is required in the same patient, it will be much less effective since the labeled antibody would be inhibited by the presence of anti-antibody antibodies. The use of a compound having a simple chemical structure which binds selectively to lymphocytes would avoid these types of problems.

The subject matter of the present invention is precisely radiopharmaceutical products using complexes having a simple chemical structure which do not give rise to the above-mentioned disadvantages.

DESCRIPTION OF THE DISCLOSURE

The subject matter of the present invention is a radiopharmaceutical product characterized in that it contains a radioactive metal complex meeting the formula:

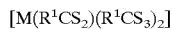

in which M is chosen from among $^{99m}$Tc, $^{186}$Re and $^{188}$Re, and R$^1$ represents an alkyl, cycloalkyl, aralkyl or aryl group, which may or may not be substituted by one or more substituents chosen from among the halogen atoms, the hydroxyl group, the alkyl groups and the alcoxy groups.

In this radiopharmaceutical product, the radioactive metal M which may be $^{99m}$Tc for diagnosis, or $^{186}$Re or $^{188}$Re for therapy, is coordinated by an assembly of non-homogeneous sulfured ligands, namely a dithiocarboxylate ligand $(R^1CS_2)^-$ and two trithioperoxycarboxylate ligands $(R^1CS_3)^-$. In this structure, the radioactive metal is in M$^{3+}$ form.

The document: Inorganic Chemistry, 1997, vol. 36, pages 6144–6145 [5] describes a rhenium complex having the same type of structure but which is not obtained from $^{186}$Re or $^{188}$Re. It is therefore not a radiopharmaceutical product.

In the structure of the complexes of the invention, the R$^1$ groups of the sulfured ligands may be alkyl, cycloalkyl, aralkyl or aryl aliphatic groups. These groups may be non-substituted or substituted by one or more substituents chosen from among the halogen atoms, fluorine for example, the hydroxyl group, the alkyl groups and the alcoxy groups.

The alkyl groups used for R$^1$ may be linear or branched groups at $C_1$ to $C_{15}$, preferably groups having 3 to 13 carbon atoms.

The cycloalkyl groups used for R$^1$ preferably have 3 to 7 carbon atoms, for example 6 carbon atoms.

The aryl groups used for R$^1$ may be of phenyl or naphthyl type.

The aralkyl groups used for R$^1$ may be of $C_6H_5(CH_2)_n$ type in which n ranges from 1 to 3, preferably n equals 1 or 2.

Preferably, in accordance with the invention, the R$^1$ group is an aryl, aralkyl or cyclohexyl group that is optionally substituted.

Advantageously, when R$^1$ is an aryl group, it is chosen from among the phenyl groups, phenyl substituted by a methyl, ethyl, butyl, ethoxy, methoxy or hydroxyl group, phenyl substituted by a fluorine atom, phenyl substituted by three methyl groups, naphthyl and naphthyl substituted by a methyl group.

When R$^1$ is an aralkyl group, this is advantageously the benzyl or phenethyl group.

A further purpose of the invention is a method for preparing a radiopharmaceutical product containing a radioactive metal complex having the formula:

$$[M(R^1CS_2)(R^1CS_3)_2]$$

in which M is chosen from among $^{99m}$Tc, $^{186}$Re and $^{188}$Re, and $R^1$ represents an alkyl, cycloalkyl, aralkyl or aryl group, which may or may not be substituted by one or more substituents chosen from among the halogen atoms, the hydroxyl group, the alkyl groups and the alcoxy groups, which consists of causing a salt of formula $(MO_4)^-Z_1^+$, in which M is as defined above and $Z_1$ is a pharmaceutically acceptable cation, to react with a reducing agent, and of adding to the reaction mixture a dithiocarboxylate of formula $(R^1CS_2)^-Z_2^+$ in which $R^1$ is as defined above and $Z_2^+$ represents a pharmaceutically acceptable cation.

The pharmaceutically acceptable cations used for $Z_1$ may be ions of alkali or alkaline earth metals, for example Na.

The pharmaceutically acceptable cations used for $Z_2$ may be chosen from among $MgX^+$ in which X is a halogen atom such as Br or Cl, the quaternary ammonium cations, and the ions of alkaline earth metals such as Na.

The quaternary ammonium cations may for example be of $NR_4$ type, in which R is an alkyl group, methyl for example. It is also possible to use quaternary ammonium cations of piperidinium type having the formula $C_5H_{10}ONH_2^+$.

In the method of the invention, the reducing agent used may be of various types. In particular a reducing agent may be used which is made up of a tin salt associated with a complexing agent having complexing properties for tin that are greater than those of dithiocarboxylate. This complexing agent may be of phosphonate, polyphosphate and polyaminocarboxylic acid type. By way of example of such complexing agents, mention may be made of pyrophosphates of ammonium or of an alkali or alkaline earth metal, glucoheptonates of ammonium or of an alkali or alkaline earth metal, diethylene triaminopentacetates of ammonium or of an alkali metal, ethylene diaminotetracetates of ammonium or of an alkali or alkaline earth metal, 1,2-diaminopropane-N,N,N',N'-tetracetates of ammonium or of an alkali or alkaline earth metal, gluconates of ammonium or of an alkali or alkaline earth metal, methylene diphosphonates of ammonium or of an alkali or alkaline earth metal, hydroxymethylene diphosphonates of ammonium or of an alkali or alkaline earth metal, citrates of ammonium or of an alkali or alkaline earth metal.

By way of example, it is possible in the method of the invention to use a tin salt made up of tin chloride associated with a complexing agent chosen from among calcium gluconate and 1,2-diaminopropane-N,N,N'N'-tetracetic acid.

According to the invention it is also possible to used reducing agents made up of triphenylphosphine or one of its derivatives associated with hydrochloric acid.

As an example of derivative of triphenylphosphine, mention may be made of sodium triphenylphosphine-tri-meta-sulfonate $P(C_6H_4SO_3)_3Na_3$.

In the method of the invention, the metal M initially at oxidation state 7 is reduced to oxidation state 3, while part of the dithiocarboxylate ligand is oxidized to trithioperoxycarboxylate.

The quantities of reducing agent used with this method are chosen in relation to the quantity of pertechnetate or perrhenate initially added.

In respect of $^{99m}$Tc pertechnetate, for activities ranging from 30 MBq to 4 GBq, the quantities of reducing agent used may range from 0.01 to 1 mg for $SnCl_2$, $2H_2O$, in the presence of an excess of complexing agent relative to the tin chloride.

When a triphenylphosphine is used as reducing agent, the quantities used are in the order of 0.1 to 5 mg for pure triphenylphosphine, and 0.2 to 10 mg for sodium triphenylphosphine trisulfonate. With these reducing agents, an aqueous solution of HCl is added to obtain $1.10^{-2}$ to $1.10^{-1}$ mol/L of HCl in the reaction medium.

Despite the similarity in the chemical properties of pertechnetate and perrhenate, it is known that for the reduction reaction, the latter ion requires greater quantities of reducing agent than those used for the pertechnetate ion.

In addition, when the radioactive metal is $^{186}$rhenium, an isotope having low specific activity, the quantity of perrhenate used is greater to obtain the same activity; therefore, to reduce this species, greater quantities of reducing agent are used than for the isotope $^{188}$rhenium.

Therefore, 0.1 to 5 mg of reducing agent may be used for $SnCl_2$, $2H_2O$, from 0.1 to 10 mg for pure triphenylphosphine, and from 0.2 to 20 mg for sodium triphenylphosphine trisulfonate.

A sufficient quantity of dithiocarboxylate, preferably dissolved in physiological serum, is then added to the reaction medium. The reaction of the ligand with the pertechnetate or perrhenate is conducted under heat, for example at a temperature of 100° C.

A further purpose of the invention is a kit for the preparation of a radiopharmaceutical product containing a radioactive metal complex having the formula:

$$[M(R^1CS_2)(R^1CS_3)_2]$$

in which M is chosen from among $^{99m}$Tc, $^{186}$Re and $^{188}$Re, and $R^1$ represents an alkyl, cycloalkyl, aralkyl or aryl group, which may or may not be substituted by one or more substituents chosen from among the halogen atoms, the hydroxyl group, the alkyl groups and the alcoxy groups, characterized in that it comprises:
  a first bottle containing
    a) a tin salt associated with a complexing agent, or
    b) a triphenylphosphine and hydrochloric acid, and
  a second bottle containing dithiocarboxylate with the formula $(R^1CS_2)^-Z_2^+$ in which $R^1$ is as defined above and $Z_2$ is a pharmaceutically acceptable cation.

According to one first embodiment of the kit, the first bottle comprises tin chloride $SnCl_2$, $2H_2O$ associated with a complexing agent chosen from among calcium gluconate and 1,2-diaminopropane-N,N,N',N'-tetracetic acid.

According to a second embodiment of the kit, the first bottle contains triphenylphosphine or sodium triphenylphosphine-trisulfonate, and hydrochloric acid.

The radiopharmaceutical products described above which selectively attach themselves to lymphocytes, may be used in compositions for the diagnosis of inflammatory processes when M is $^{99m}$Tc, or in compositions for the radiotherapy of malignant lymphomas if M is $^{186}$Re or $^{6188}$Re.

Other characteristics and advantages of the invention will become clearer on reading the following examples which are evidently given for illustration purposes and are not restrictive.

DETAILED DESCRIPTION OF THE EMBODIMENTS

EXAMPLE 1

Preparation of $^{99m}$Tc[$S_2$CPh)($S_3$CPh)$_2$] in Which ph Represents the Phenyl Group In this example, tin chloride is used as reducing agent and 1,2-diaminopropane-N,N,N',N'-tetracetic acid (PDTA) as complexing agent, and the starting material is pertechnetate [$^{99m}TcO_4$]$^-$ in the form of a sodium salt, in physiological serum solution, which is eluted from a $^{99}Mo/^{99m}Tc$ generator.

To a sterile bottle, containing 0.1 mg $SnCl_2$, $2H_2O$ and 5 or 10 mg 1,2-diaminopropane-N,N,N'N'-tetracetic acid dissolved in 1 mL of physiological serum, is added 0.4 to 0.8 GBq of the sodium pertechnetate taken from the generator. The mixture is vortex homogenized and then heated to 100° C. for 15 minutes. 20.0 mg of sodium dithiobenzoate $PhCS_2^-Na^-$, dissolved in 1.0 mL of physiological serum, is then added to the hot mixture and the solution is heated to 100° C. for an additional 45 minutes.

In this way a radiopharmaceutical product is obtained which is analyzed by thin layer radiochromatography or by high performance liquid chromatography.

EXAMPLE 2

Preparation of [$^9Tc(S_2CPh)(S_3CPh)_2$]

In this example, the reduction of pertechnetate is conducted using triphenylphosphine and HCl.

To a sterile bottle containing 0.2 mL of an ethanol solution of triphenylphosphine at $2.10^{-2}$ mol/L, 0.2 mL of an aqueous solution of HCl at 0.1 mol/L and 0.6 mL physiological serum, is added 0.4 to 0.8 GBq of sodium pertechnetate taken from the generator. The mixture is vortex homogenized and then heated to 100° C. for 15 minutes. 20.0 mg of sodium dithiobenzoate $PhCS_2Na$ is then added under heat, dissolved in 1.0 ml of physiological serum, and heating of the solution is continued to 100° C. for an additional 30 minutes.

In this way a radiopharmaceutical product is obtained whose radiochemical purity is 71%.

EXAMPLE 3

Preparation of $^{99}Tc(S_2CPh)(S_3CPh)_2$]

In this example, sodium triphenylphosphine-tri-meta-sulfonate TPPTS is used having the formula: [$P(C_6H_4SO_3)_3$]Na, in the presence of hydrochloric acid.

To a sterile bottle containing 0.2 mL of an aqueous solution of TPPTS at $2.10^{-2}$ mol L−1, 0.2 mL of an aqueous solution of HCl at 0.1 mol.L−1 and 0.6 mL of physiological serum, is added 0.4 to 0.8 GBq of sodium pertechnetate taken from the generator. The mixture is vortex homogenized, and is then heated to 100° C. for 15 minutes. 20.0 mg of sodium dithiobenzoate, $PhCS_2Na_4$, dissolved in 1.0 physiological serum, is then added under heat and heating of the solution is continued at 100° C. for an additional 30 minutes.

In this way a radiopharmaceutical product is obtained whose radiochemical purity is 94%.

EXAMPLE 4

Preparation of [$^{99m}Tc(PhCS_3)_2(PhCS_2)$]

In this example, tin chloride is used as reducing agent, associated with calcium gluconate acting as complexing agent.

To a bottle containing 75.0 mg calcium gluconate, 0.75 mg $SnCl_2.2H_2O$ and 25.0 mg sodium chloride dissolved in 10 mL physiological serum, 0.4 to 0.8 GBq of pertechnetate is added taken from the generator. The mixture is shaken at room temperature for 10 minutes, then 20 mg sodium dithiobenzoate $PhCS_2Na^+$, dissolved under heat in 1.0 mL physiological serum, is added and the solution is heated to 100° C. for an additional 15 minutes.

A radiopharmaceutical product is obtained whose radiochemical purity is greater than 95%.

Operating conditions, radiochemical purity RCP and the Rf values obtained by thin layer chromatography TLC of $SiO_2$ using a petroleum ether/$CH_2Cl_2$ mixture (70/30) as eluent are given in table 2.

EXAMPLES 5 TO 31

Following the operating mode of example 4, radiopharmaceutical products are prepared containing the complexes [$^{99m}Tc(R^1CS_3)_2(R^1CS_2)$] of table 1 using the dithiocarboxylates also given in table 1.

Radiopharmaceutical products are thus obtained which contain technetium complexes. The radiochemical purity and Rf values of the products obtained are given in table 1.

In the same manner, rhenium complexes are prepared that are similar to the $^{99m}Tc$ complexes of examples 1 to 4, 9, 11, 13, 15, 17, 19, 23 and 25 using potassium or sodium perrhenate as starting material.

EXAMPLE 32

Labeling of Blood Cells

The radiopharmaceuticals of table I (2 mCi; 74 MBq) are incubated in 3 mL of a fresh sample of human blood for 10 minutes under slow shaking. The blood composition depends upon each sample taken from healthy volunteers (average composition: $1.6\pm0.3.10^{10}$ Red Globules (RG) and $2.2\pm0.3.10^7$ White Globules (WG) with $1.2\pm0.3.10^7$ Polymorphs (57±9%) and $0.7\pm0.3.10^7$ Lymphocytes (35±4%)]. Non-bound radioactivity is removed by successive washings (2×10 mL of RPMI culture medium 1640) of 10 minutes at 600 g. The yield of cell labeling is determined in a CAP-INTEC CRC 120 activimeter. Cell viability is controlled by the Trypan blue exclusion test.

The results obtained, namely the labeling yield (Yield) and the percentages of activity in the separated fractions are given in tables 3 to 5.

If these results are compared with those obtained under the same conditions with the complex nitrurobis(N-ethoxy-N-ethyldithiocarbamato)technetium-99m called [$^{99m}TcN(NOET)_2$]described in FR-A-2 698 272 [6], which is known to achieve leukocyte labeling, of granulocytes in particular, reproducibility is good.

EXAMPLE 33

Labeling of Lymphocytes

In this example, verification is made of the selectivity of the complexes of the invention for lymphocytes.

In a first experiment, a separation of the blood constituents is made on a double density Polymorphprep® gradient.

Whole blood from healthy volunteers is labeled with 2 mCi of [$^{99m}Tc(ArCS_3)_2(ArCS_2)$] following the method described above. The blood constituents are then separated by the Polymorphprep® double density gradient into two separate fractions: lymphocytes and polymorphs/erythrocytes. The whole blood, diluted in 2–3 mL RPMI, is initially delicately placed on the Polymorphprep® gradient and then centrifuged (300 g, 20 min, 37° C.). After separation, the radioactivity counted in each fraction reveals the distribution profile of the radiopharmaceutical. Counting is made on each fraction using a MAXM Y07 00 367 counter in order to confirm cell constitution.

In a further experiment, the labeled leukocytes are separated on a double density PERCOLL gradient, which enables separation of the lymphocytes from the polymorphs and erythrocytes.

The operating mode is as follows:

Whole blood from healthy volunteers (10 mL) is labeled with 10 mCi of [$^{99m}Tc(ArCS_3)_2(ArCS_2)$] following the above-described method. The blood constituents are separated, after two RPMI washings, via the PERCOLL double density gradient into three separate fractions: lymphocytes/polymorphs/erythrocytes (sedimentation). Sedimentation of the labeled blood sample is conducted at 37° C. for 20 minutes. The supernatant is recovered then centrifuged for 10 min at 1250 rev.min$^{-1}$. The cell deposit diluted in 2.5 mL RPMI is delicately placed on the PER-COLL gradient then centrifuged a further time (1300 rev.min$^{-1}$, 15 min, 37° C.). After separation and 2 RPMI washings (900 rev.min$^{-1}$, 2 min), the radioactivity counted in each fraction reveals the distribution profile of the radiopharmaceutical product. Counting is made for each fraction with a MAXM Y07 367 counter in order to confirm cell constitution. Cell viability is controlled by the Trypan blue exclusion test.

The results obtained show that more than 95% of the labeled leukocytes, which were identified by separation on a Polymorphprep® gradient, are lymphocytes.

The radiopharmaceutical products of the invention therefore show strong selectivity for lymphocytes compared with other leukocytes, using whole blood labeling.

Cited References

[1]: J. Martin-Conin, Radiolabeled Blood Elements, Plenum Press, New York, 1994, pages 261 to 265.

[2]: J. Martin-Conin, Radiolabeled Blood Elements, Plenum Press, New-York, 1994, pages 267 to 271.

[3]: Nuclear Medicine & Biology, 1997, volume 24, pages 439–445.

[4]: Nuclear Medicine & Biology, 1999, volume 26, pages 225–231.

[5]: Inorganic Chemistry, 1997, vol 36, pp. 6144–6145.

[6]: FR-A-2 698 272.

TABLE 1

| Ex | Complex | Dithiocarboxylate | Rf | RCP(%) |
|---|---|---|---|---|
| 1 | [$^{99m}$Tc(PhCS$_3$)$_2$ (PhCS$_2$)] | PhCS$_2$ Na | 0.62 | <20 |
| 2 | [$^{99m}$Tc(PhCS$_3$)$_2$ (PhCS$_2$)] | PhCS$_2$ Na | 0.62 | 71 |
| 3 | [$^{99m}$Tc(PhCS$_3$)$_2$ (PhCS$_2$)] | PhCS$_2$ Na | 0.62 | 94 |
| 4 | [$^{99m}$Tc(PhCS$_3$)$_2$ (PhCS$_2$)] | PhCS$_2$ Na | 0.62 | >95 |
| 5 | [$^{99m}$Tc(4-MePhCS$_3$)$_2$(4-MePhCS$_2$)] | 4-MePhCS$_2$(C$_5$H$_{10}$NH$_2$)] | 0.68 | 85 |
| 6 | [$^{99m}$Tc(4-MePhCS$_3$)$_2$(4-MePhCS$_2$)] | 4-MePhCS2Na | 0.68 | 83 |
| 7 | [$^{99m}$Tc(4-EtPhCS$_3$)$_2$(4-EtPhCS$_2$)] | 4-EtPhCS$_2$(C$_5$H$_{10}$NH$_2$)] | 0.76 | 91 |
| 8 | [$^{99m}$Tc(4-EtPhCS$_3$)$_2$(4-EtPhCS$_2$)] | 4-EtPhCS$_2$Na | 0.76 | 90 |
| 9 | [$^{99m}$Tc(2-EtPhCS$_3$)$_2$(2-EtPhCS$_2$)] | 2-EtPhCS$_2$(C$_5$H$_{10}$NH$_2$)] | 0.79 | 89 |
| 10 | [$^{99m}$Tc(2-EtPhCS$_3$)$_2$(2-EtPhCS$_2$)] | 2-EtPhCS$_2$Na | 0.79 | 88 |
| 11 | [$^{99m}$Tc(4-nBuPhCS$_3$)$_2$(4-nBuPhCS$_2$)] | 4-nBuPhCS$_2$(C$_5$H$_{10}$NH$_2$)] | 0.88 | 88 |
| 12 | [$^{99m}$Tc(4-nBuPhCS$_3$)$_2$(4-nBuPhCS$_2$)] | 4-nBuPhCS$_2$Na | 0.88 | 90 |
| 13 | [$^{99m}$Tc(4-EtOPhCS$_3$)$_2$(4-EtOPhCS$_2$)] | 4-EtOPhCS$_2$(C$_5$H$_{10}$NH$_2$) | 0.43 | 82 |
| 14 | [$^{99m}$Tc(4-EtOPhCS$_3$)$_2$(4-EtOPhCS$_2$)] | 4-EtOPhCS$_2$Na | 0.43 | 89 |
| 15 | [$^{99m}$Tc(3-MeOPhCS$_3$)$_2$(3-MeOPhCS$_2$)] | 3-MeOPhCS$_2$ (C$_5$H$_{10}$NH$_2$) | 0.34 | 48 |
| 16 | [$^{99m}$Tc(3-MeOPhCS$_3$)$_2$(3-MeOPhCS$_2$)] | 3-MeOPhCS$_2$Na | 0.34 | 55 |
| 17 | [$^{99m}$Tc(4-OHPhCS$_3$)$_2$(4-OHPhCS$_2$)] | 4-OHPhCS$_2$ (C$_5$H$_{10}$NH$_2$) | 0 | 98 |
| 18 | [$^{99m}$Tc(4-OHPhCS$_3$)$_2$(4-OHPhCS$_2$)] | 4-OHPhCS$_2$Na | 0 | 97 |
| 19 | [$^{99m}$Tc(4-FPhCS$_3$)$_2$ (4-FPhCS$_2$)] | 4-FPhCS$_2$ (C$_5$H$_{10}$NH$_2$) | 0.73 | 95 |
| 20 | [$^{99m}$Tc(4-FPhCS$_3$)$_2$ (4-FPhCS$_2$)] | 4-FPhCS$_2$Na | 0.75 | 95 |
| 21 | [$^{99m}$Tc(2,4,5-Me$_3$PhCS$_3$)$_2$(2,4,5-Me$_3$PhCS$_2$)] | 2,4,5-Me$_3$PhCS$_2$ (C$_5$H$_{10}$NH$_2$) | 0.83 | 91 |
| 22 | [$^{99m}$Tc(2,4,5-Me$_3$PhCS$_3$)$_2$(2,4,5-Me$_3$PhCS$_2$)] | 2,4,5-Me$_3$PhCS$_2$ Na | 0.84 | 97 |
| 23 | [$^{99m}$Tc(1-naphCS$_3$)$_2$(1-naphCS$_2$)] | 1-naphCS$_2$ (C$_5$H$_{10}$NH$_2$) | 0.58 | 97 |
| 24 | [$^{99m}$Tc(1-naphCS$_3$)$_2$(1-naphCS$_2$)] | 1-naphCS$_2$Na | 0.58 | 95 |
| 25 | [$^{99m}$Tc(2-Me-naphCS$_3$)$_2$(2-Me-naphCS$_2$)] | 2-Me-naphCS$_2$ (C$_5$H$_{10}$NH$_2$) | 0.65 | 91 |
| 26 | [$^{99m}$Tc(2-Me-naphCS$_3$)$_2$(2-Me-naphCS$_2$)] | 2-Me-naphCS$_2$ MgBr | 0.65 | 75 |
| 27 | [$^{99m}$Tc(PhCH$_2$CS$_3$)$_2$(PhCH$_2$CS$_2$)] | PhCH$_2$CS$_2$ MgCl | 0.80 | 63 |
| 28 | [$^{99m}$Tc(PhCH$_2$CH$_2$CS$_3$)$_2$(PhCH$_2$CH$_2$CS$_2$)] | PhCH$_2$CH$_2$CS$_2$ (C$_5$H$_{10}$NH$_2$) | 0.80 | 69 |
| 29 | [$^{99m}$Tc(PhCH$_2$CH$_2$CS$_3$)$_2$(PhCH$_2$CH$_2$CS$_2$)] | PhCH$_2$CH$_2$CS$_2$ MgBr | 0.55 | 21 |
| 30 | [$^{99m}$Tc(C$_6$H$_{12}$CS$_3$)$_2$CS$_2$(C$_6$H$_{12}$CS$_2$)] | C$_6$H$_{12}$CS$_2$ (C$_5$H$_{10}$NH$_2$) | 0.68 | 61 |
| 31 | [$^{99m}$Tc(C$_6$H$_{12}$CS$_3$)$_2$CS$_2$(C$_6$H$_{12}$CS$_2$)] | C$_6$H$_{12}$CS$_2$ MgBr | 0.66 | 36 |

Ph = 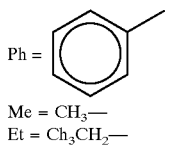

Me = CH$_3$—
Et = CH$_3$CH$_2$—

TABLE 1-continued

| Ex | Complex | Dithiocarboxylate | Rf | RCP(%) |
|---|---|---|---|---| n-Bu = CH₃—(CH₂)₃— naph = 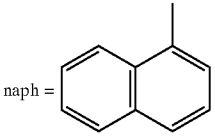

TABLE 2

| Ex | Reducing agent | T (° C.) | T (min) | Rf | RCP (%) |
|---|---|---|---|---|---|
| Ex 1 | SnCl₂/PDTA | 100 | 45 | 0.62 | <20 |
| Ex 2 | HCl/PPH₃ | 100 | 30 | 0.62 | 71 |
| Ex 3 | HCl/TPPTS | 100 | 30 | 0.62 | 94 |
| Ex 4 | ScCl₃/Gluconate | 100 | 15 | 0.62 | >95 |

TABLE 3

Effect of the lipid affinity of ligands $ArCS_2NH_2C_5H_{10}$ on the labeling of whole blood

| Examples | 5 | 7 | 9 | 11 | 13 | 15 | 17 | 19 | 21 |
|---|---|---|---|---|---|---|---|---|---|
| Yield (±3%) | 98 | 93 | 72 | 97 | 99 | 99 | 93 | 99 | 90 |
| Cell separation on whole blood (activity %) | | | | | | | | | |
| Medium | 0 | 2 | 2 | — | — | — | 2 | 1 | 1 |
| Leukocytes | 80 | 83 | 72 | 46 | 70 | 73 | 85 | 80 | 82 |
| Polymorphprep ® | 3 | 3 | 2 | 1 | 1 | 2 | 1 | 4 | 2 |
| Erythrocytes | 17 | 12 | 24 | 53 | 29 | 25 | 12 | 15 | 15 |

TABLE 4

| Examples | 6 | 8 | 10 | 12 | 14 | 16 | 18 | 20 | 22 |
|---|---|---|---|---|---|---|---|---|---|
| Yield (±3%)ᵇ | 95 | 99 | 92 | 100 | 97 | 98 | 93 | 91 | 95 |
| Cell separation on whole blood (activity %) | | | | | | | | | |
| Medium | — | 1 | 2 | 1 | — | 3 | 1 | — | — |
| Leukocytes | 78 | 85 | 76 | 66 | 75 | 79 | 89 | 84 | 78 |
| Polymorphprep ® | 2 | — | 2 | 4 | 3 | 2 | 3 | 4 | 2 |
| Erythrocytes | 20 | 14 | 22 | 29 | 22 | 16 | 7 | 12 | 20 |

TABLE 5

Effect of the aromaticity of ligands $ArCS_2X$ (X = Na or $NH_2C_5H_{10}$) on the labeling of whole blood

| Examples | 23 | 25 | 27 | 29 | 30 | 24 | 26 | 28 | 31 |
|---|---|---|---|---|---|---|---|---|---|
| Yield (±3%)ᵇ | 71 | 96 | 88 | 43 | 97 | 74 | 85 | 91 | 63 |
| Cell separation on whole blood (activity %) | | | | | | | | | |
| Medium | 6 | 1 | 1 | 1 | 2 | 1 | 4 | 2 | — |
| Leukocytes | 43 | 85 | 77 | 35 | 75 | 53 | 79 | 80 | 68 |
| Polymorphprep ® | 5 | 4 | 10 | 6 | 10 | — | 2 | 2 | 3 |
| Erythrocytes | 46 | 10 | 11 | 58 | 13 | 46 | 15 | 16 | 29 |

What is claimed is:

1. Radiopharmaceutical product suitable for the selective labeling of lymphocytes in whole blood, characterized in that it contains a radioactive metal complex meeting the formula:

$$[M(R^1CS_2)(R^1CS_3)_2]$$

in which M is chosen from among $^{99m}Tc$, $^{186}Re$ and $^{188}Re$, and $R^1$ represents an alkyl, cycloalkyl, aralkyl or aryl group, which may or may not be substituted by one or more substituents chosen from among the halogen atoms, the hydroxyl group, the alkyl groups and the alkoxy groups.

2. Radiopharmaceutical product according to claim 1, in which the aryl group is the phenyl group or the naphthyl group.

3. Radiopharmaceutical product according to claim 2, in which $R^1$ is the phenyl group.

4. Radiopharmaceutical product according to claim 2, in which $R^1$ is chosen from among the phenyl groups substituted by a methyl, ethyl, butyl, ethoxy, methoxy or hydroxyl group, phenyl substituted by a fluorine atom and phenyl substituted by three methyl groups.

5. Radiopharmaceutical product according to claim 2, in which $R^1$ is the naphthyl group or the naphthyl group substituted by a methyl group.

6. Radiopharmaceutical product according to claim 1, in which $R^1$ is the cyclohexyl, benzyl or phenethyl group.

7. Method for preparing a radiopharmaceutical product containing a radioactive metal complex with the formula:

$$[M(R^1CS_2)(R^1CS_3)_2]$$

in which M is chosen from among $^{99m}Tc$, $^{186}Re$ and $^{188}Re$, and $R^1$ represents an alkyl, cycloalkyl, aralkyl or aryl group, which may or may not be substituted by one or more substituents chosen from among the halogen atoms, the hydroxyl group, the alkyl groups and the alkoxy groups, which consists of:

causing a salt having the formula:

$$(MO_4)^-Z_1^+$$

in which M is as defined above and $Z_1$ is a pharmaceutically acceptable cation, to react with a reducing agent, and adding to the reaction mixture a dithiocarboxylate having the formula:

$$(R^1CS_2)^-Z_2^+$$

in which $R^1$ is as defined above and $Z_2$ represents a pharmaceutically acceptable cation.

8. Method according to claim 7, in which $Z_2$ represents a cation chosen from among $MgX^+$ in which X is a halogen atom, an alkali metal ion, a quaternary ammonium cation or the piperidinium cation.

9. Method according to claim 7, in which the reducing agent is a tin salt associated with a complexing agent.

10. Method according to claim 9, in which the tin salt is tin chloride and the complexing agent is calcium gluconate or 1,2-diaminopropane-N,N,N',N'-tetracetic acid.

11. Method according to claim 7, in which the reducing agent is triphenylphosphine or sodium triphenylphosphine trimetasulfonate associated with hydrochloric acid.

12. Composition for the diagnosis of inflammatory processes containing a radiopharmaceutical product according to any of claims 1 to 6, in which M is $^{99m}$Tc.

13. Composition for the radiotherapy of malignant lymphomas containing a radiopharmaceutical product according to any of claims 1 to 6, in which M is $^{186}$Re or $^{188}$Re.

14. Kit for the preparation of a radiopharmaceutical product containing a radioactive metal complex having the formula:

[M(R$^1$CS$_2$)(R$^1$CS$_3$)$_2$]

in which M is chosen from among $^{99m}$Tc, $^{186}$Re, $^{188}$Re, and R$^1$ represents an alkyl, cycloalkyl, aralkyl or aryl group, which may or may not be substituted by one or more substituents chosen from among the halogen atoms, the hydroxyl group, the alkyl groups and the alkoxy groups, characterized in that it comprises:

a first bottle containing:

a) a tin salt associated with a complexing agent, or b) a triphenylphosphine and hydrochloric acid, and a second bottle containing a dithiocarboxylate with the formula: (R$^1$CS$_2$)$^-$Z$_2^+$ in which R$^1$ is as defined above and Z$_2$ represents a pharmaceutically acceptable cation.

15. Kit according to claim 14, characterized in that the first bottle contains tin chloride SnCl$_2$, 2H$_2$O associated with a complexing agent chosen from among calcium gluconate and 1,2-diaminopropane-N,N,N',N'-tetracetic acid.

16. Kit according to claim 14, in which the first bottle contains triphenylphosphine or sodium triphenylphosphine-trisulfonate, and hydrochloric acid.

17. The radiopharmaceutical product of claim 1, where M is $^{99m}$Tc and R$^1$ is phenyl.

* * * * *